(12) United States Patent  
Rizoiu et al.

(10) Patent No.: US 7,970,030 B2  
(45) Date of Patent: Jun. 28, 2011

(54) DUAL PULSE-WIDTH MEDICAL LASER WITH PRESETS

(75) Inventors: Ioana M. Rizoiu, San Clemente, CA (US); Dmitri Boutoussov, Dana Point, CA (US)

(73) Assignee: Biolase Technology, Inc., Irvine, CA (US)

( * ) Notice: Subject to any disclaimer, the term of this patent is extended or adjusted under 35 U.S.C. 154(b) by 183 days.

(21) Appl. No.: 12/368,266

(22) Filed: Feb. 9, 2009

(65) Prior Publication Data

US 2009/0141752 A1 Jun. 4, 2009

Related U.S. Application Data

(63) Continuation-in-part of application No. 11/191,594, filed on Jul. 27, 2005, now Pat. No. 7,630,420, which is a continuation-in-part of application No. 11/033,032, filed on Jan. 11, 2005, now abandoned, which is a continuation-in-part of application No. 11/203,400, filed on Aug. 12, 2005, now abandoned.

(60) Provisional application No. 60/591,933, filed on Jul. 27, 2004, provisional application No. 60/601,415, filed on Aug. 13, 2004.

(51) Int. Cl.  
*H01S 3/00* (2006.01)

(52) U.S. Cl. ............... 372/38.04; 372/38.06; 372/25; 372/30; 372/31; 372/38.02; 372/70; 606/10; 606/11

(58) Field of Classification Search ............... 372/38.06, 372/38.04, 25, 30, 31, 38.02, 70; 606/10; 606/11  
See application file for complete search history.

(56) References Cited

U.S. PATENT DOCUMENTS

| 3,051,905 | A |   | 8/1962  | Haynes |
|-----------|---|---|---------|--------|
| 3,051,906 | A | * | 8/1962  | Haynes ........................ 327/105 |
| 3,515,938 | A | * | 6/1970  | Morse .......................... 315/240 |
| 3,578,986 | A | * | 5/1971  | McGuffin et al. ............. 327/397 |
| 3,679,863 | A |   | 7/1972  | Houldcroft et al. |
| 3,679,998 | A |   | 7/1972  | Dahlinger |
| 3,711,725 | A | * | 1/1973  | Johannessen ................. 307/108 |
| 3,914,648 | A |   | 10/1975 | Friedman et al. |
| 3,991,296 | A |   | 11/1976 | Kojima et al. |
| 4,005,333 | A |   | 1/1977  | Nichols |

(Continued)

FOREIGN PATENT DOCUMENTS

DE 3840126 A1 5/1990

(Continued)

OTHER PUBLICATIONS

Cook, "Pulse Forming Network Investigation", Aug. 1975, Thesis at Texas Tech University.*

(Continued)

*Primary Examiner* — Jessica T Stultz  
*Assistant Examiner* — Joshua King  
(74) *Attorney, Agent, or Firm* — Stout, Uxa, Buyan & Mullins, LLP (57) ABSTRACT

A medical laser device is described that generates a laser beam controllable with presets as to pulse duration, pulse repetition rate, power and energy per pulse. The device also provides presets with respect to water and air outputs. Parametric values for power, pulse duration, pulse repetition rate, and energy per pulse as well as for water and air settings may be programmed by an end user and stored as presets.

20 Claims, 8 Drawing Sheets

U.S. PATENT DOCUMENTS

| | | |
|---|---|---|
| 4,087,705 A | 5/1978 | Barnes |
| 4,276,518 A | 6/1981 | Ferguson |
| 4,550,275 A | 10/1985 | O'Loughlin |
| 4,724,299 A | 2/1988 | Hammeke |
| 4,770,811 A | 9/1988 | Myers |
| 4,826,431 A | 5/1989 | Fujimura et al. |
| 4,862,888 A | 9/1989 | Yessik |
| 4,908,030 A | 3/1990 | Linkow et al. |
| 4,910,438 A | 3/1990 | Farnsworth |
| 4,913,142 A | 4/1990 | Kittrell et al. |
| 4,931,047 A | 6/1990 | Broadwin et al. |
| 4,985,027 A | 1/1991 | Dressel |
| 5,086,378 A | 2/1992 | Prince |
| 5,092,773 A | 3/1992 | Levy |
| 5,092,864 A | 3/1992 | Hayes et al. |
| 5,102,410 A | 4/1992 | Dressel |
| 5,151,029 A | 9/1992 | Levy |
| 5,199,870 A | 4/1993 | Steiner et al. |
| 5,221,561 A | 6/1993 | Flicstein et al. |
| 5,237,331 A | 8/1993 | Henderson et al. |
| 5,242,454 A | 9/1993 | Gundlach et al. |
| 5,263,950 A | 11/1993 | L'Esperance, Jr. |
| 5,267,856 A | 12/1993 | Wolbarsht et al. |
| 5,313,481 A | 5/1994 | Cook et al. |
| 5,318,562 A | 6/1994 | Levy et al. |
| 5,334,019 A | 8/1994 | Goldsmith et al. |
| 5,374,266 A | 12/1994 | Kataoka et al. |
| 5,388,988 A | 2/1995 | Goisser et al. |
| 5,401,171 A | 3/1995 | Paghdiwala |
| 5,409,376 A | 4/1995 | Murphy |
| 5,498,935 A | 3/1996 | McMahan et al. |
| 5,552,675 A | 9/1996 | Lemelson |
| 5,554,172 A | 9/1996 | Horner et al. |
| 5,570,182 A | 10/1996 | Nathel et al. |
| 5,611,797 A | 3/1997 | George |
| 5,694,046 A | 12/1997 | Hillerich et al. |
| 5,723,864 A | 3/1998 | Atkinson et al. |
| 5,729,562 A | 3/1998 | Birx et al. |
| 5,741,247 A | 4/1998 | Rizoiu et al. |
| 5,755,751 A | 5/1998 | Eckhouse |
| 5,764,672 A | 6/1998 | Ukita et al. |
| 5,785,521 A | 7/1998 | Rizoiu et al. |
| 5,820,627 A | 10/1998 | Rosen et al. |
| 5,825,958 A | 10/1998 | Gollihar et al. |
| 5,828,803 A | 10/1998 | Eckhouse |
| 5,869,805 A | 2/1999 | Beyer et al. |
| 6,080,148 A | 6/2000 | Damasco et al. |
| 6,083,218 A | 7/2000 | Chou |
| 6,106,516 A | 8/2000 | Massengill |
| 6,118,521 A | 9/2000 | Jung et al. |
| 6,193,711 B1 | 2/2001 | Connors et al. |
| 6,223,987 B1 | 5/2001 | Knowles et al. |
| 6,231,567 B1 | 5/2001 | Rizoiu et al. |
| 6,254,597 B1 | 7/2001 | Rizoiu et al. |
| 6,288,499 B1 | 9/2001 | Rizoiu et al. |
| 6,315,772 B1 | 11/2001 | Marchitto et al. |
| 6,350,123 B1 | 2/2002 | Rizoiu et al. |
| 6,389,193 B1 | 5/2002 | Kimmel et al. |
| 6,449,301 B1 | 9/2002 | Wu et al. |
| 6,512,782 B1 | 1/2003 | Hsia et al. |
| 6,561,803 B1 | 5/2003 | Rizoiu et al. |
| 6,567,582 B1 | 5/2003 | Rizoiu et al. |
| 6,669,685 B1 | 12/2003 | Rizoiu et al. |
| 6,701,181 B2 | 3/2004 | Tang et al. |
| 6,878,899 B2 | 4/2005 | Smart |
| 6,902,290 B2 | 6/2005 | Watts et al. |
| 7,097,639 B1 | 8/2006 | Almeida |
| 7,415,050 B2 | 8/2008 | Rizoiu et al. |
| 2002/0149324 A1 | 10/2002 | Rizoiu et al. |
| 2003/0069567 A1* | 4/2003 | Eckhouse et al. ............... 606/9 |
| 2003/0100824 A1 | 5/2003 | Warren et al. |
| 2003/0227953 A1* | 12/2003 | Hsia et al. ..................... 372/53 |
| 2005/0137655 A1 | 6/2005 | MacFarland |
| 2005/0143792 A1 | 6/2005 | Jay |
| 2006/0020309 A1 | 1/2006 | Altshuler et al. |

FOREIGN PATENT DOCUMENTS

| | | |
|---|---|---|
| DE | 4138468 | 3/1993 |
| EP | 0181199 | 5/1986 |
| EP | 0912833 | 9/1986 |
| EP | 0454312 A2 | 10/1991 |
| EP | 0454312 A3 | 10/1991 |
| EP | 96 41657 | 12/1995 |
| GB | 2 023 330 | 12/1979 |
| GB | 2297610 | 8/1996 |
| JP | 5945092 | 3/1984 |
| JP | 5200045 A | 8/1993 |
| JP | 5506601 A | 9/1993 |
| JP | 11511386 A | 10/1999 |
| JP | 200301465 | 1/2003 |
| JP | 2003070722 A | 3/2003 |
| WO | 9004358 A1 | 5/1990 |
| WO | 97 07928 A3 | 3/1997 |
| WO | 9707928 | 3/1997 |
| WO | 97 45165 | 4/1997 |

OTHER PUBLICATIONS

Cook, "Pulse Forming Network Investigation", Aug. 1975, Thesis at Texas Tech University.*
Supplementary European Search Report, EP 05711358 (PCT/US2005/000852), mailed Feb. 8, 2010.
International Search Report, Jun. 30, 2008, PCT/US08/051963.
International Search Report, May 23, 2008, PCT/US08/051967.
International Search Report & Written Opinion, Sep. 2, 2005, PCT/US05/00849.
International Search Report & Written Opinion, Jul. 31, 2006, PCT/US06/00989.
International Search Report & Written Opinion, Oct. 25, 2006, PCT/US05/28891.
International Search Report, Dec. 10, 1998, PCT/US98/12357.
Written Opinion, Apr. 15, 1999, PCT/US98/12357.
European Search Report, Jun. 6, 2005, EP 05 07 5231.
Partial European Search Report, Apr. 6, 2000, EP 98 92 9060.
T.S. Fahlen, Efficient Quarter-Joule KrF Laser with Corona Prelonization, IEEE Journal of Quantum Electronics, vol. QE-15, No. 5, pp. 311-312. May 5, 1979.
Bernard Grob, Basic Electronics, Glencoe division of Macmillan/McGraw-Hill, pp. 690-681. 1989.
New Laser—Matter Interaction Concept to Enhance Tissue Cutting Efficiency by Ioana M. Rizoiu and Larry G. DeShazer, published in SPIE col. 2134A Laser-Tissue Interaction V(1994)/309.
Rizoiu, Ioana and Levy, Guy C. "Efficiency of Bone Ablation with an Nd:YAG Laser Beam Delivered with a Cooling Spray" SPIE vol. 1882 Laser-Tissue Interaction IV (1993), pp. 316-321.
Rizoiu, Ioana and Levy, Guy C. "Morphological Changes of Dentin and Enamel after Ablation with an Experimental Laser System" SPIE vol. 2128, pp. 282-288.

* cited by examiner

DUAL PULSE-WIDTH MEDICAL LASER WITH PRESETS

CROSS-REFERENCE TO RELATED APPLICATIONS

This application is a continuation-in-part of U.S. application Ser. No. 11/191,594, filed Jul. 27, 2005 now U.S. Pat. No. 7,630,420 and entitled DUAL PULSE-WIDTH MEDICAL LASER, the entire contents of which are incorporated herein by reference. U.S. application Ser. No. 11/191,594 claims the benefit of U.S. Provisional Application No. 60/591,933, filed Jul. 27, 2004 and entitled DUAL PULSE-WIDTH MEDICAL LASER, the entire contents of which are incorporated herein by reference. U.S. application Ser. No. 11/191,594 is a continuation-in-part of U.S. application Ser. No. 11/033,032, filed Jan. 11, 2005 now abandoned and entitled ELECTROMAGNETIC ENERGY DISTRIBUTIONS FOR ELECTROMAGNETICALLY INDUCED DISRUPTIVE CUTTING, the entire contents of which are incorporated herein by reference. This application is also a continuation-in-part of U.S. application Ser. No. 11/203,400, filed Aug. 12, 2005 now abandoned and entitled DUAL PULSE-WIDTH MEDICAL LASER WITH PRESETS, the entire contents of which are incorporated herein by reference. U.S. application Ser. No. 11/203,400 claims the benefit of U.S. Provisional Application No. 60/601,415, filed Aug. 13, 2004 and entitled DUAL PULSE-WIDTH MEDICAL LASER WITH PRESETS, the entire contents of which are incorporated herein by reference. U.S. application Ser. No. 11/203,400 is a continuation-in-part of U.S. application Ser. No. 11/033,032, filed Jan. 11, 2005 now abandoned and entitled ELECTROMAGNETIC ENERGY DISTRIBUTIONS FOR ELECTROMAGNETICALLY INDUCED DISRUPTIVE CUTTING, the entire contents of which are incorporated herein by reference.

BACKGROUND OF THE INVENTION

1. Field of the Invention

The present invention relates generally to electromagnetic energy emitting devices and, more particularly, to pulsed medical treatment laser devices.

2. Description of Related Art

A variety of electromagnetic energy generating architectures have existed in the prior art. A solid-state laser system, for example, generally comprises a laser rod for emitting coherent light and a source for stimulating the laser rod to emit the coherent light. Flashlamps are typically used as stimulation sources for middle infrared lasers between 2.5 microns ($\mu m$) and 3.5 $\mu m$, such as Er, Cr:YSGG and Er:YAG laser systems. The flashlamp is driven by a flashlamp current, which comprises a predetermined pulse shape and a predetermined frequency.

The flashlamp current drives the flashlamp at the predetermined frequency, to thereby produce an output flashlamp light distribution having substantially the same frequency as the flashlamp current. This output flashlamp light distribution from the flashlamp drives the laser rod to produce coherent light at substantially the same predetermined frequency as the flashlamp current.

Medical applications, such as those requiring the excision of soft human tissue, may in some instances require or benefit from two opposite tissue effects. The first effect may relate to laser cutting of tissue with controlled hemostasis, minimal to no bleeding, and attenuated or eliminated charring of cut surfaces. The second effect may relate to laser cutting with bleeding in order, for example, to stimulate post-operative healing when tissue is brought together. The second effect can be particularly important or relevant, for example, in grafting applications.

Prior art methods of generating these first and second effects can include employing distinctly different devices for each type of tissue cutting. Some prior art methods of performing first and second effect procedures may include employing systems capable of generating different wavelengths of electromagnetic energy. For example, wavelengths of about 1 $\mu m$ and about 3 $\mu m$ may be generated using $CO_2$ and Erbium type lasers, respectively. Overhead time and effort that may be required in switching between two medical devices can be disadvantages of this approach. Extra time and attendant discomfort from a point of view of a patient undergoing such procedures may represent additional disadvantages.

A need exists in the prior art for laser devices capable of rapidly and efficiently transitioning between varying characteristics or modes of operation, to facilitate, for example, different desired cutting effects or procedures such as for facilitating both hemostatic-type and bleeding-type tissue cutting effects

SUMMARY OF THE INVENTION

An exemplary implementation of the method present invention addresses these needs by providing first and second high voltage outputs from a single power supply. A laser-pumping source (e.g., a flashlamp) also can be provided, the laser-pumping source being capable of exciting a laser that may be used for cutting tissue. The first and second high voltage outputs drive respective first and second pulse-forming networks capable of generating respective first and second pulse outputs that pump the laser-pumping source according to the exemplary implementation of the method. Pulses produced by the first pulse-forming network may be relatively short, and pulses produced by the second pulse-forming network may be relatively long.

Another embodiment of the present invention comprises an electromagnetic energy emitting device, which, according to an exemplary embodiment, may comprise a medical laser device, wherein the electromagnetic energy-emitting device is capable of emitting a sequence of electromagnetic pulses having first durations and second durations, wherein the electromagnetic energy-emitting device is adapted to store presets specifying combinations of electromagnetic pulses having first durations and second durations and wherein the apparatus is capable of cutting tissue. One embodiment of the medical electromagnetic energy device can comprise a controller capable of storing presets, which may include parameters that control operation of the medical electromagnetic energy device. Examples of parameters that may be stored as presets can include power, pulse duration, pulse repetition rate, energy per pulse, a water setting, and an air setting. Another embodiment of the medical electromagnetic energy device can include a user input panel through which a user can modify and save presets.

While the apparatus and method has or will be described for the sake of grammatical fluidity with functional explanations, it is to be expressly understood that the claims, unless expressly formulated under 35 U.S.C. 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. 112 are to be accorded full statutory equivalents under 35 U.S.C. 112.

Any feature or combination of features described herein are included within the scope of the present invention provided that the features included in any such combination are not mutually inconsistent as will be apparent from the context, this specification, and the knowledge of one skilled in the art. For purposes of summarizing the present invention, certain aspects, advantages and novel features of the present invention are described herein. Of course, it is to be understood that not necessarily all such aspects, advantages or features will be embodied in any particular embodiment of the present invention. Additional advantages and aspects of the present invention are apparent in the following detailed description and claims that follow.

DETAILED DESCRIPTION OF THE INVENTION

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims. It is to be understood and appreciated that the process steps and structures described herein do not cover a complete architecture and process flow for operation of electromagnetic energy (e.g., laser) devices. The present invention may be practiced in conjunction with various structures and techniques that are conventionally used in the art, and only so much of the commonly practiced items are included herein as are necessary to provide an understanding of the present invention. The present invention has applicability in the field of electromagnetic treatment devices in general. For illustrative purposes, however, the following description pertains to a medical laser device and a method of operating the medical laser device to perform tissue treatments and surgical functions.

Figure 1:
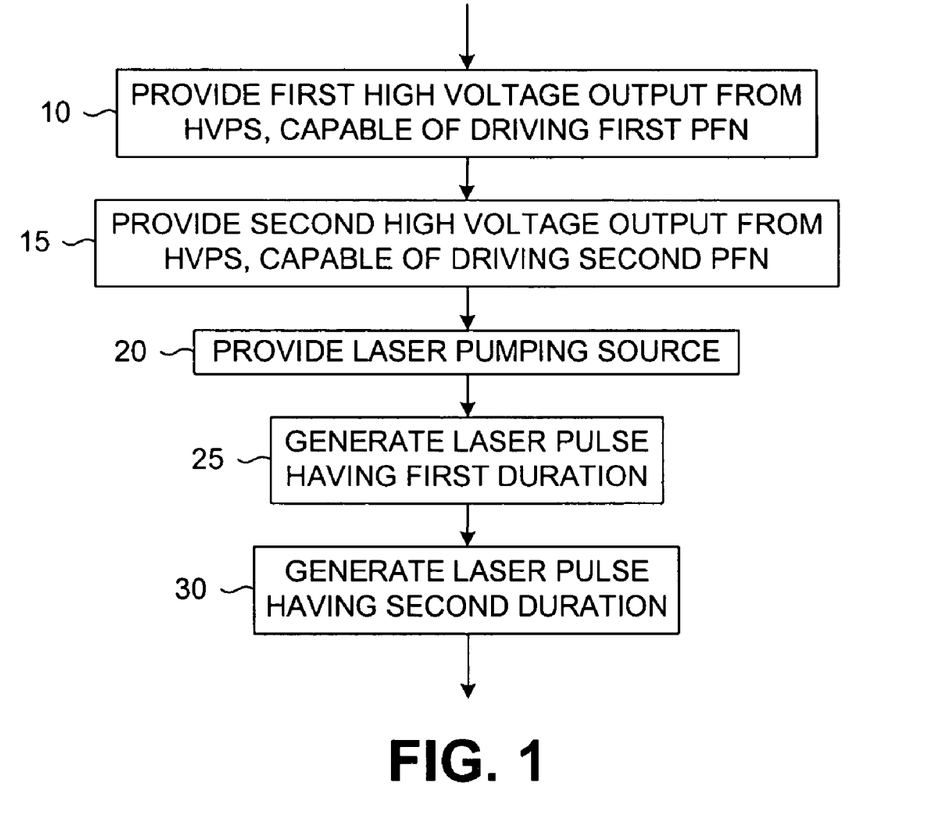
FIG. 1 is a flow diagram describing an implementation of the method of the present invention.

Referring more particularly to the drawings, FIG. 1 is a flow diagram describing an implementation of the method of the present invention. This implementation of the method provides a first high voltage output from a high voltage power supply (HVPS) at step 10. The first high voltage output is capable of driving a first pulse-forming network (PFN). A second high voltage output from the HVPS is provided at step 15. The second high voltage output is capable of driving a second pulse-forming network. An exemplary embodiment of the high voltage outputs described herein can provide about 1500 volts from the first high voltage output and about 500 volts from the second high voltage output. A pumping source, such as a laser-pumping source, is further provided at step 20 according to the implementation. In a representative embodiment, the laser-pumping source can comprise a flashlamp capable of stimulating emission of coherent light by a laser device such as, for example, an Er:YSGG or Er, Cr:YSGG solid state laser. At step 25 of the implementation, an electromagnetic energy (e.g., laser) pulse having a first duration (i.e., width) is generated by pumping the laser-pumping source with the first pulse-forming network output. Similarly, at step 30 a laser pulse having a second duration may be generated by pumping the laser-pumping source with the second pulse-forming network output.

Figure 2:
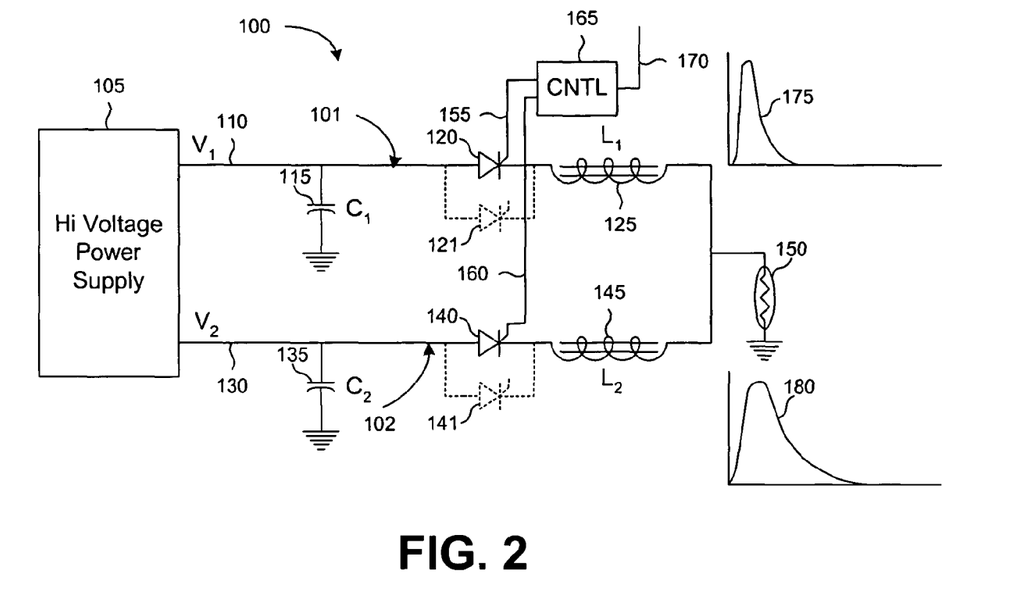
FIG. 2 is a schematic diagram illustrating an embodiment of a dual pulse-width flashlamp driving circuit according to the present invention.

An example of a circuit capable of driving a flashlamp from first and second high voltage outputs is described below with reference to FIG. 2. A relatively detailed implementation of the circuit of FIG. 2 is disclosed in FIGS. 2p and 3p of U.S. Provisional Application No. 60/591,933, filed Jul. 27, 2004 and entitled DUAL PULSE-WIDTH MEDICAL LASER, the entire contents of which are incorporated herein by reference to the extent compatible or modifiable by one skilled in the art to be compatible with any aspect or modified aspect of the present invention. An Er:YSGG or Er, Cr:YSGG solid state laser, which is capable of generating electromagnetic energy having a wavelength in a range of about 2.70 microns ($\mu$m) to 2.80 $\mu$m, typically 2.78 $\mu$m, may be driven with the architecture of this circuit. Parameters of the first and second pulse-forming networks may be adjusted to produce, respectively, pulses having relatively short and long durations. In a typical embodiment, relatively short pulses having durations of, for example, about 140 microseconds ($\mu$s) are produced by the first pulse-forming network, and relatively long pulses having durations of, for example, about 400 $\mu$s are produced by the second pulse-forming network. Repetition rates for the pulses may range, for example, from about 1 to 50 pulses/second.

A partial schematic diagram of an embodiment of a dual pulse-width analog flashlamp driving circuit 100 according to the present invention is shown in FIG. 2, comprising a high voltage power supply 105 capable of producing dual, i.e., respective first and second, high voltage outputs 110 and 130 using methods known to those skilled in the art. The illustrated embodiment of the dual pulse-width analog flashlamp driving circuit 100 further comprises a first pulse-forming network 101 and a second pulse-forming network 102 connected to respective first and second high voltage outputs 110 and 130. First and second pulse-forming networks 101 and 102 are further connected to a flashlamp 150 that may function as a pumping source for a laser (not shown).

The first pulse-forming network 101 in the illustrated embodiment comprises a first capacitor 115, a first switching transistor 120, (for example, an insulated gate bipolar transistor (IGBT)), and a first inductor 125. The first capacitor 115 is connected between the first high voltage output 110 and ground. The first high voltage output 110 further is connected to the first inductor 125 through the first switching transistor 120, and the flashlamp 150 is electrically connected between the first inductor 125 and ground. The first pulse-forming network 101 and the second pulse-forming network 102 may be similar in form to a circuit such as that shown in FIG. 3 of the above-referenced U.S. application Ser. No. 11/033,032 entitled ELECTROMAGNETIC ENERGY DISTRIBUTIONS FOR ELECTROMAGNETICALLY INDUCED MECHANICAL CUTTING. The second pulse-forming network 102, which is similar in form to the first pulse-forming network 101, comprises a second capacitor 135, a second switching transistor 140, and a second inductor 145. The second high voltage output 130 is applied to a terminal of the second capacitor 135, which has another terminal connected to ground. The second high voltage output 130 also is coupled through a second switching transistor 140 to the second inductor 145, which is connected to the flashlamp 150.

In typical embodiments of the dual pulse-width analog flashlamp driving circuit 100, first and second capacitors 115 and 135 may assume values of, respectively, about 30 microfarads (µF) to about 70 µF, with an exemplary value being about 50 µF, and about 300 µF to about 600 µF, with an exemplary value being about 400 µF. First and second capacitors may receive respective first and second high voltage outputs 110 and 130. The first high voltage output 110 in an illustrative embodiment has a value ranging from about 1200 volts to about 1500 volts at an impedance level capable of charging the first capacitor 115 at a rate of about 1500 Joules per second (J/s). The second high voltage output 130 in the embodiment may range from about 200 volts to about 500 volts at an impedance level capable of charging the second capacitor 135 at a rate of about 1 J/s. The first inductor 125 may comprise an inductance of about 30 microhenries (µH) to about 70 µH, such as a solid core inductor having a rated inductance of about 50 µH in an exemplary embodiment. The second inductor 145 may comprise an inductance of about 800 µH to about 1200 µH, such as a solid core inductor having an inductance of about 1 millihenry (mH). The flashlamp 150 may comprise a 450 to 900 torr source, such as a 700 torr source. Control signals 155 and 160 from a control device 165 may be applied to terminals of transistors 120 and 140 in order to enable operation of the first pulse-forming network 101 or the second pulse-forming network 102. Enabling the first pulse-forming network 101 may generate relatively short electromagnetic energy pulses, and enabling the second pulse-forming network 102 may generate relatively long electromagnetic energy pulses according to a typical mode of operation of the illustrated embodiment. A user input 170, which may comprise, for example, a switch on a electromagnetic energy housing or handset (not shown), may specify parameters (e.g., user adjustable parameters) such as pulse duration and/or pulse repetition rate. In certain embodiments, additional switching transistors 121 and 141, shown in phantom in FIG. 2, may be provided in order to increase current capacity of the first and second pulse-forming networks 101 and 102.

A relatively short current pulse 175 may be produced by the first pulse-forming network 101 in the embodiment of the dual pulse-width analog flashlamp driving circuit 100 illustrated in FIG. 2. The second pulse-forming network 102 may produce a relatively long current pulse 180 with parameters chosen substantially as described herein.

Figure 3:
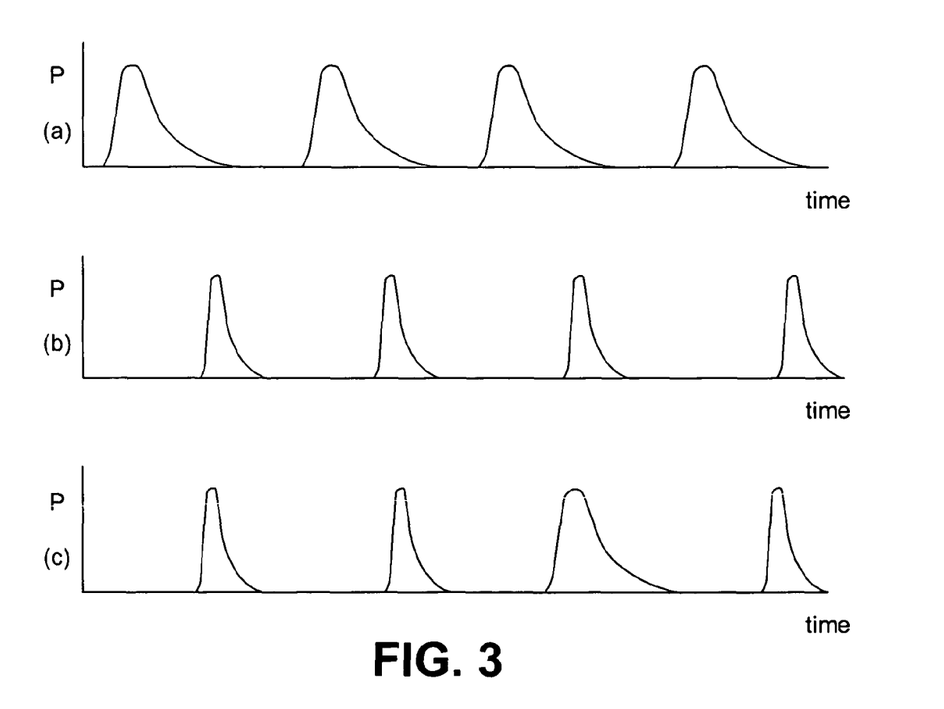
FIG. 3 is a plot depicting short, long, and mixed electromagnetic energy pulses generated by the dual pulse-width flashlamp driving circuit shown in FIG. 2 in accordance with various aspects of the present invention.

FIG. 3 is a chart illustrating three exemplary chains (a, b, c) of electromagnetic energy pulses capable of being produced by an electromagnetic energy (e.g., laser) device driven by a dual pulse-width circuit according to the present invention, such as a dual pulse-width analog flashlamp driving circuit 100 shown in FIG. 2. Chain (a) illustrates electromagnetic energy, such as laser energy, generated according to relatively long pulses. Chain (b) illustrates relatively short pulses of electromagnetic energy, such as laser energy, and chain (c) depicts a mixture of relatively long and short pulses. An end user, such as a dentist or physician, as distinguished from a manufacturer or technician, may select a type of pulse chain to be produced using, for example, a user input 170 (FIG. 2).

Long pulses generated by the embodiment illustrated in FIG. 2 may be used to achieve an objective of cutting tissue with good hemostasis, no bleeding, and no charring of a cut surface. Conversely, short pulses generated by the same embodiment may provide for cutting with bleeding in order to promote post-operative healing. In another application, short pulses may be employed in the cutting of hard tissue (e.g., tooth enamel, dentin, bone) while long pulses may be used in cutting soft tissue (e.g., periodontal, mucosa, liver, kidney) and to perform thermal modifications. Examples of long pulse and short pulse applications are described in, for example, the above-referenced U.S. Provisional Application No. 60/601,415 entitled DUAL PULSE-WIDTH MEDICAL LASER WITH PRESETS and U.S. application Ser. No. 11/033,032 entitled ELECTROMAGNETIC ENERGY DISTRIBUTIONS FOR ELECTROMAGNETICALLY INDUCED MECHANICAL CUTTING. According to certain implementations of the present invention, use of the methods and apparatus described herein are not restricted to medical (or dental) applications alone, and similar methods and apparatus contemplated by the present invention may be applied in industrial applications, such as for removing and shaping semiconductor materials.

Figure 4:
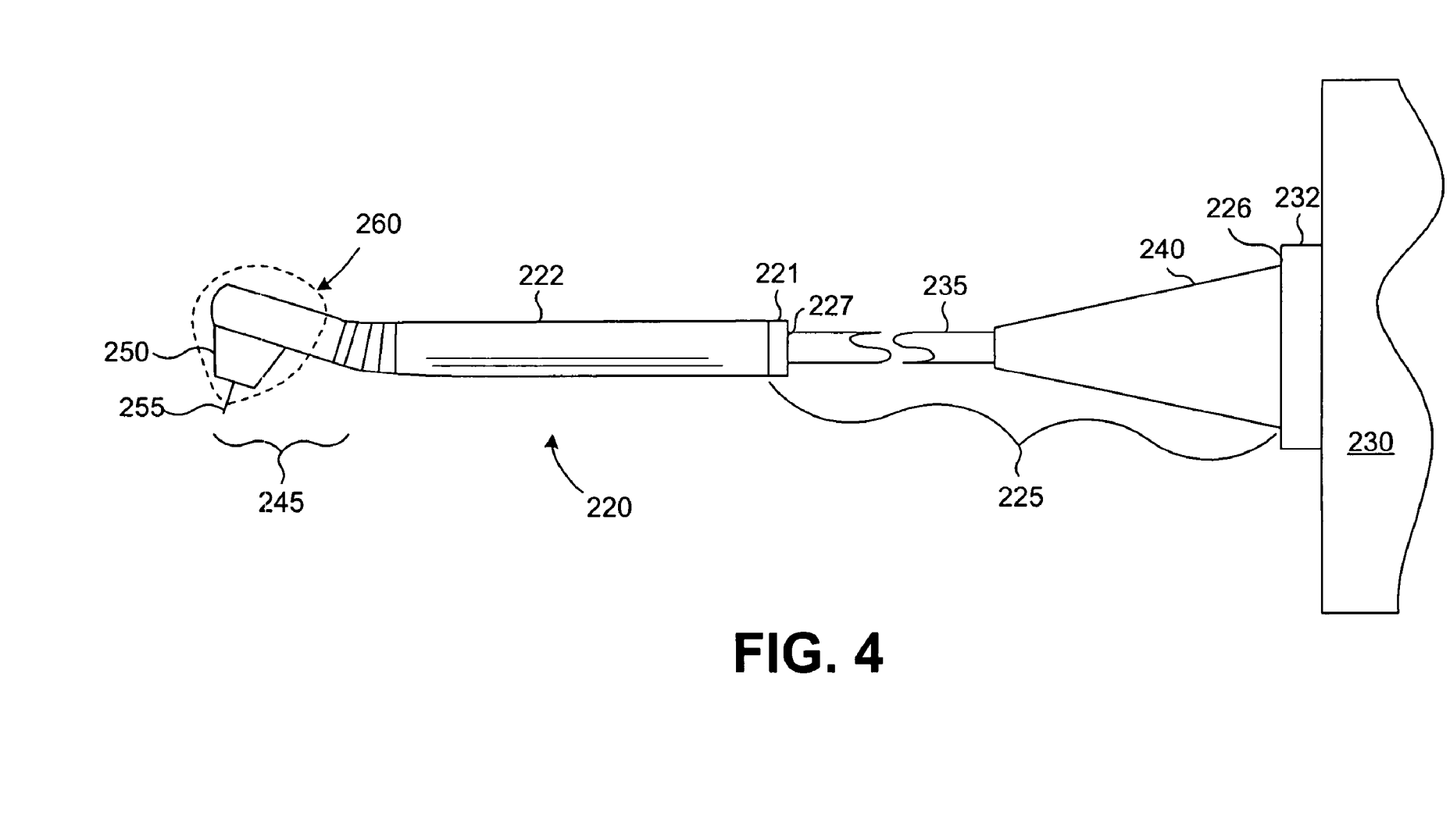
FIG. 4 is a pictorial diagram of a delivery system capable of transmitting electromagnetic energy to a treatment site in accordance to an exemplary embodiment the present invention.

FIG. 4 is a pictorial diagram of a delivery system capable of transferring electromagnetic (e.g., laser) energy to a treatment site. The illustrated embodiment comprises an electromagnetic energy (e.g., laser) handpiece 220 that connects to an electromagnetic energy (e.g., laser) base unit 230 using a linking element 225. The linking element 225 may comprise a conduit 235, which may include one or more electromagnetic energy (e.g., laser) conduits or fibers, tubing for air, tubing for water, and the like. The linking element 225 further may comprise a connector 240 that joins the conduit 235 to the electromagnetic energy base unit 230. The connector 240 may be an identification connector as is described more fully in U.S. application Ser. No. 11/192,334, filed Jul. 27, 2005 and entitled IDENTIFICATION CONNECTOR FOR A MEDICAL LASER HANDPIECE, the entire contents of which are incorporated herein by reference to the extent compatible or modifiable by one skilled in the art to be compatible with any aspect or modified aspect of the present invention. The electromagnetic energy handpiece 20 may comprise an elongate portion 222 and a handpiece tip 245, the elongate portion 222 having disposed therein a plurality of optical fibers that may connect to, or that are the same as, the optical fibers included in the conduit 235. A proximal (i.e., relatively nearer to the electromagnetic energy base unit 230) portion 221 and a distal (i.e., relatively further from the electromagnetic energy base unit 230) portion 250 may be disposed at respective proximal and distal ends of the electromagnetic energy handpiece 220. The distal portion 250 has protruding therefrom an output fiber tip 255 that is described below in more detail with reference to FIG. 5. As illustrated, the linking element 225 has a first end 226 and a second end 227. First end 226 couples to a receptacle 232 of the electromagnetic energy base unit 230. Second end 227 couples to the proximal portion 221 of the electromagnetic energy handpiece 220. The connector 240 may connect mechanically to the electromagnetic energy base unit 230 with a threaded connection to the receptacle 232.

Figures 5, 5A:
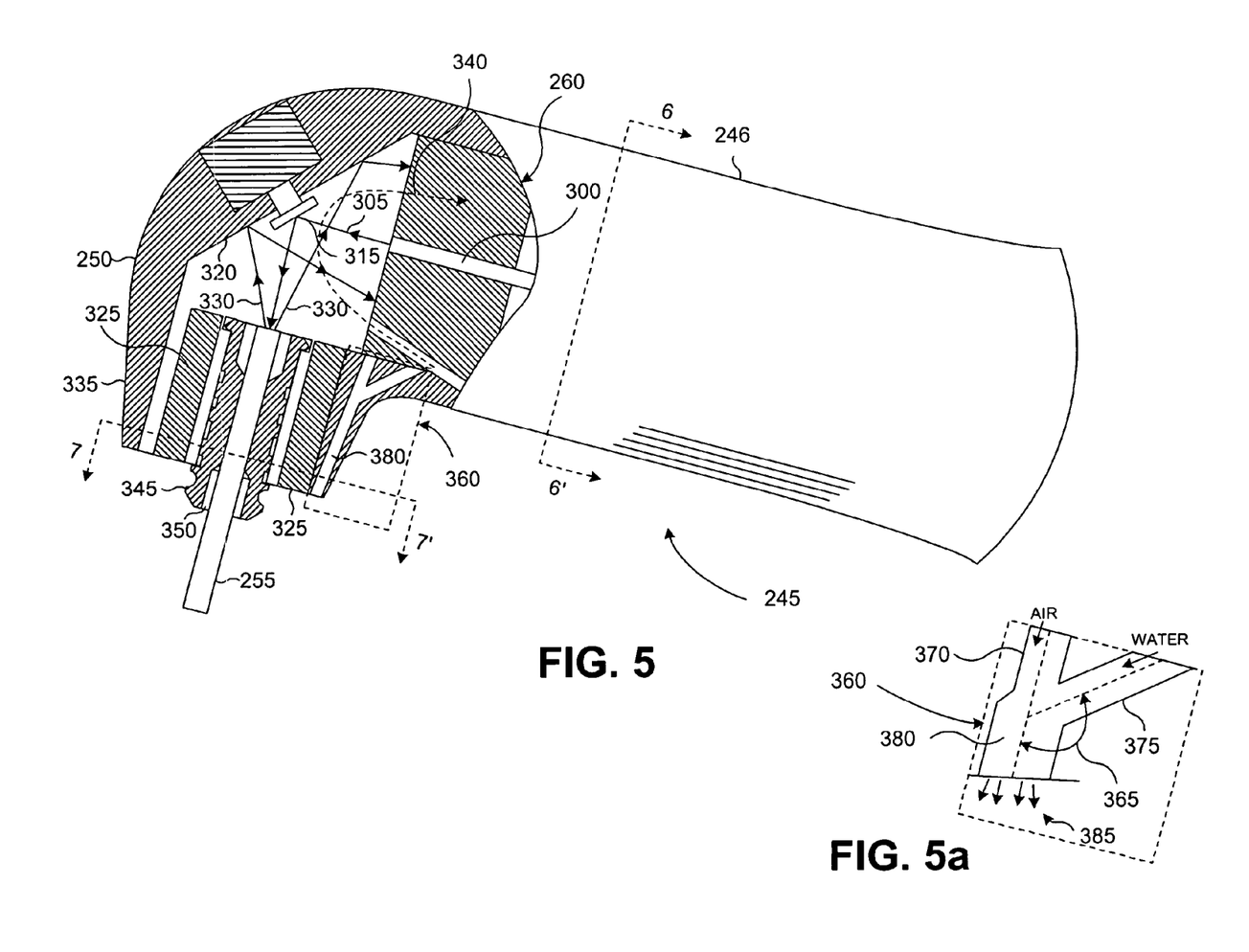
FIG. 5 is a partial cut-away diagram of a handpiece tip in accordance with an exemplary implementation of the present invention.
FIG. 5a is a detailed illustration of an embodiment of a chamber for mixing spray air and spray water in the handpiece tip of FIG. 5.

FIG. 5 is a partial cut-away diagram of a handpiece tip 245 (cf. FIG. 4) that couples with the electromagnetic energy base unit 230 through the linking element 225 and the elongate portion 222 of the electromagnetic energy handpiece 220. The illustrated embodiment, which is enclosed by an outer surface 246, may receive power or treatment electromagnetic (e.g., laser) energy from the electromagnetic energy base unit 230. Typically, the treatment electromagnetic energy is transmitted through a waveguide, such as treatment fiber 300, disposed in the elongate portion 222 and the handpiece tip 245 as described below with reference to FIG. 6. According to one embodiment, treatment electromagnetic energy 305 is received by an internal waveguide, such as treatment fiber 300, and is directed toward a first mirror 315 disposed in the distal portion 250 of the electromagnetic energy handpiece 220, whence reflected electromagnetic energy is directed toward the output fiber tip 255. Electromagnetic energy received by the output fiber tip 255 may be directed toward a target (e.g., a treatment) surface. The output fiber tip 255 may be encased in a tip ferrule or sleeve 345 that, together with the output fiber tip 255, forms a removable, interchangeable unit as is described more fully in U.S. Provisional Application No. 60/610,757, filed Sep. 17, 2004 and entitled, OUTPUT ATTACHMENTS CODED FOR USE WITH ELECTRO-MAGNETIC-ENERGY PROCEDURAL DEVICE, the entire contents of which are incorporated herein by reference to the extent compatible or modifiable by one skilled in the art to be compatible with any aspect or modified aspect of the present invention.

Figure 6:
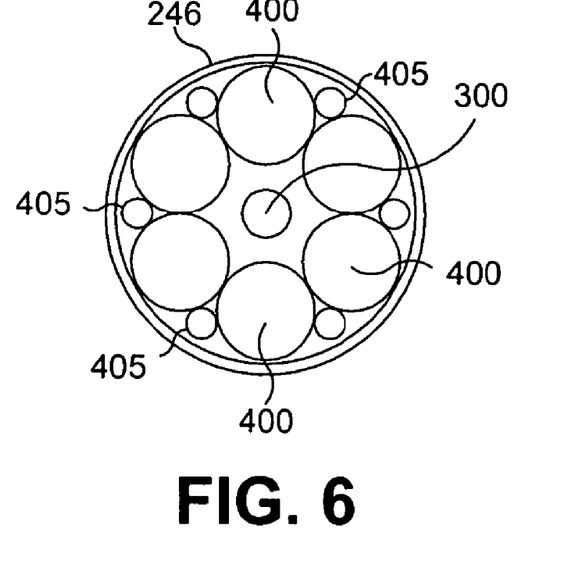
FIG. 6 is a cross-sectional view of the handpiece tip of FIG. 4 taken along line 6-6' in accordance with an aspect of the present invention.

FIG. 6 is a cross-sectional diagram of a portion of an embodiment of the handpiece tip 245, the cross-section being taken along a line 6-6' of FIG. 5. The electromagnetic energy fiber 300 may carry electromagnetic energy that is directed toward first mirror 315 as already described. According to another embodiment, additional fibers, such as illumination fibers 400, may carry another form of electromagnetic energy, such as visible light, blue light, and the like, which electromagnetic energy may be directed toward a second mirror 320 (FIG. 5), whence the electromagnetic energy is directed toward a plurality of tip waveguides 325 (FIG. 5) disposed in a housing 335 as is more particularly described below with reference to FIG. 7. Another implementation of the present invention receives reflected light from a target surface, a first portion 330 of the reflected light being received from the output fiber tip 255, and a second portion of the reflected light (not shown) being received from the plurality of tip waveguides 325. The reflected light, including the first portion 330, may be received by second mirror 320, which directs the reflected light to feedback fibers 405 (FIG. 6) disposed in an interior of the handpiece tip 245. The feedback fibers 405 may transmit the reflected light to the electromagnetic energy base unit 230 where the reflected light can be analyzed as is described, for example, in U.S. application Ser. No. 11/203,677, filed Aug. 12, 2005 and entitled LASER HANDPIECE ARCHITECTURE AND METHODS and U.S. application Ser. No. 11/203,399, filed Aug. 12, 2005 and entitled CARIES DETECTION USING TIMING DIFFERENTIALS BETWEEN EXCITATION AND RETURN PULSES, the entire contents of both which are incorporated herein by reference to the extent compatible or modifiable by one skilled in the art to be compatible with any aspect or modified aspect of the present invention.

Figure 7:
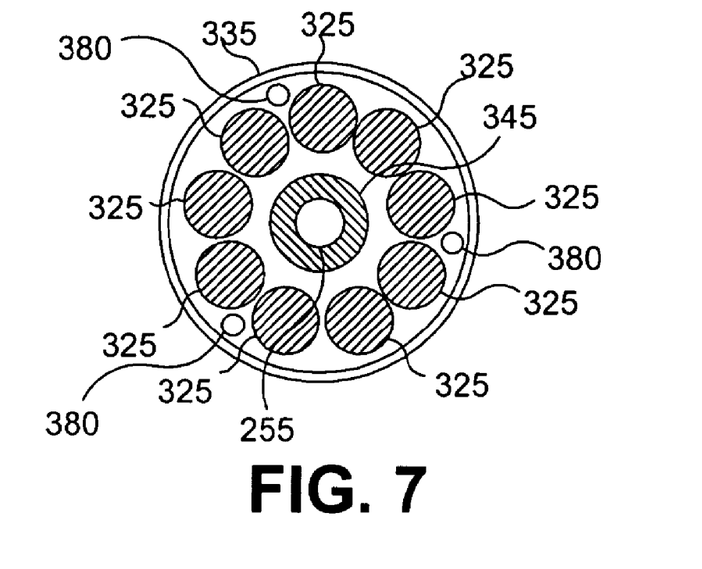
FIG. 7 is a cross-sectional diagram of a handpiece tip taken along line 7-7' in FIG. 4 according to another aspect of the present invention.

FIG. 7 is a cross-sectional diagram taken through a housing portion 335 of the electromagnetic energy handpiece tip 245 of FIG. 5. The illustrated embodiment depicts an output fiber tip 255 surrounded by a tip ferrule or sleeve 345, and, optionally, glue that fills a cavity 350 around the output fiber tip 255 to hold the output fiber tip 255 in place. The housing portion 335 may comprise tip waveguides 325 circularly disposed about the output fiber tip 255 that may receive illumination light from the second mirror 320 (FIG. 5) and direct the illumination light to a target as described above. In certain embodiments, a plurality of fluid outputs 380 may be disposed in the housing portion 335 of the handpiece tip 245, the fluid outputs 380 being configured to direct, for example, a mixture of air and water to a target.

A detailed illustration of an embodiment of a chamber for mixing spray air and spray water in the handpiece tip 245 is shown in FIG. 5a. As illustrated, the mixing chamber comprises an air intake 370 connected to, for example, tubing (not shown) that connects to, and receives air from, a spray air connection in the connector 240 (FIG. 2). Similarly, a water intake 375 may connect to tubing (also not shown) that connects to and receives water from a spray water connection in the connector 240 (FIG. 4). The air intake 370 and the water intake 375, which may have circular cross-sections about 250 µm in diameter, join at an angle 365 that may approximate 110° in a typical embodiment. Mixing may occur or begin to occur in a neighborhood where the air intake 370 and water intake 375 join, and a spray (e.g., atomized) mixture 385 of water and air may be ejected through a fluid output 380. The embodiment illustrated in FIG. 7 depicts three fluid outputs 380. These fluid outputs may, for example, correspond to, comprise parts of, or comprise substantially all of, any of the fluid outputs described in U.S. application Ser. No. 11/042,824, filed Jan. 24, 2005 and entitled ELECTROMAGNETICALLY INDUCED CUTTER AND METHOD, the entire contents of which are incorporated herein by reference to the extent compatible or modifiable by one skilled in the art to be compatible with any aspect or modified aspect of the present invention. The fluid outputs 380 may, as illustrated in FIGS. 4 and 7, have a circular cross-section measuring about 350 µm in diameter.

One aspect of the present invention, as outlined in User Manual for a Waterlase® All-Tissue Laser for Dentistry (referenced herein as "the incorporated Waterlase® User Manual"), the entire contents of which are incorporated herein by reference, includes programmed parameter values referred to herein as presets, the presets being applicable to various surgical procedures. Presets may be programmed at a time of manufacture of a device, in which case the presets may be referred to as pre-programmed presets. Alternatively or additionally, presets may be generated or modified and stored by an end user. Table 2 of the incorporated Waterlase® User Manual is reproduced herein as Table 1 and includes examples of pre-programmed presets for general hard and soft tissue procedures.

TABLE 1

Suggested Presets for General Hard and Soft Tissue Procedures

| Preset # | Procedure | Power (Watts) | Rep Rate (Hz) | Energy Per pulse (mJ) | Water Setting (%) | Air Setting (%) |
|---|---|---|---|---|---|---|
| 1 | Enamel Cutting | 6.0 | 20 | 300 | 75 | 90 |
| 2 | Dentin Cutting | 4.0 | 20 | 200 | 55 | 65 |
| 3 | Soft Tissue Cutting (thin tissue, small incisions) | 1.5 | 20 | 75 | 7 | 11 |
| 4 | Soft Tissue Coagulation | 0.75 | 20 | 37.5 | 0 | 11 |

According to exemplary embodiments, a plurality of presets (e.g., programmed settings for one or more of power, repetition rate, pulse duration, pulse energy, and settings for air and water as shown in Table 1) may be established. Although not shown in the table, an aspect of the present invention comprises the inclusion of pulse duration as one of the presets. The plurality of presets may be generated at a time of manufacture and stored in the electromagnetic energy base unit 230 (FIG. 4). In addition to the pre-programmed preset values for general hard and soft tissue procedures set forth in Table 1, combinations of customized values of parameters can be stored in the electromagnetic energy base unit 230 as new presets. According to one implementation of the present invention, each preset can store a pulse duration (e.g., a long-pulse mode having pulse durations selectable or variable from about 650 to about 1000 μs or a short-pulse mode having a pulse duration of about 140 μs), such as a currently-active pulse duration, as a parameter and further can store one or more additional parameters from a group including power in watts (W), pulse repetition rate in hertz (Hz), energy per pulse in millijoules (mJ), water setting (%) and air setting (%).

Figure 8:
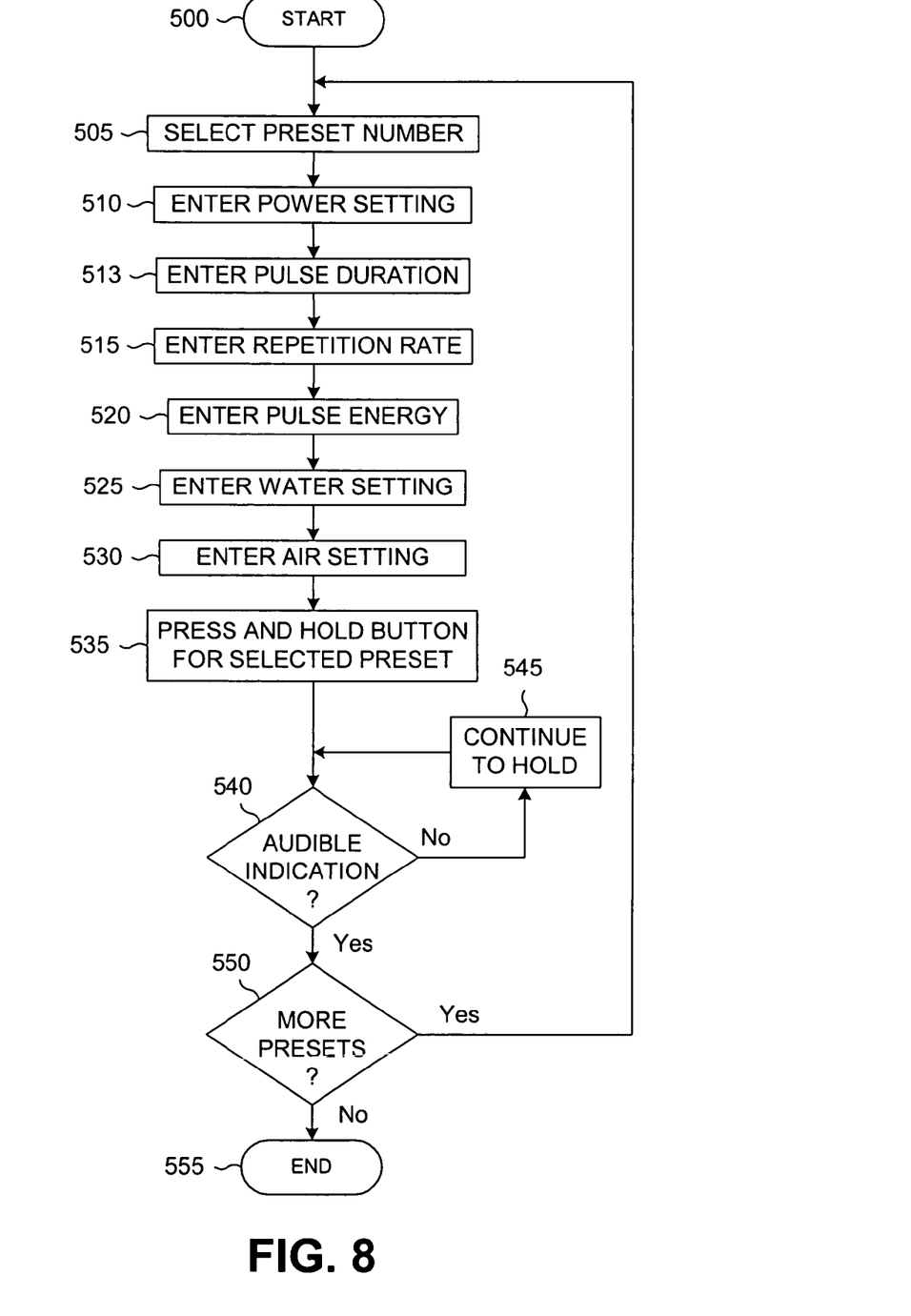
FIG. 8 is a flow diagram summarizing an implementation of a method of modifying and saving specified values as presets in accordance with the present invention.

FIG. 8 is a flow diagram summarizing an implementation of a method of modifying and saving predetermined or preferred values as presets. The illustrated implementation commences at step 500 and can continue by selecting a preset number at step 505 after which a power setting can be entered at step 510. According to one embodiment, a user interface on an electromagnetic energy base unit comprises a plurality of buttons, including preset buttons, and a display, whereby an end user, as distinguished from a manufacturer or technician, may select a preset by pressing a button associated with the selected preset. A power setting, which may relate, for example, to an emitted power level of an electromagnetic energy (e.g., laser) beam, may be entered by pressing buttons (e.g., power up/down buttons) on the keypad in a manner known to those skilled in the art. Similarly, values for one or more of pulse duration, repetition rate, pulse energy, water setting, and air setting may be entered at respective steps 513, 515, 520, 525, and 530, for example, by pressing up/down buttons corresponding to respective values for pulse duration, repetition rate, pulse energy, water setting, and air setting.

After the values (e.g., one or more of the values) have been entered, an embodiment of an electromagnetic energy housing, such as laser housing 230 (FIG. 4)), then stores the entered preset values in response to an end user pressing and holding the selected preset button at step 535 while waiting at step 540 for an audible notification (e.g., a beep) that the entered preset value or values have been stored. Until a beep is heard (e.g., about two to three seconds in one embodiment), the end user continues to hold the selected preset button at step 545 and to wait for the audible indication. After the audible indication is heard, the implementation continues at step 550 with a decision, which may be made by the end user, as to whether more presets are to be stored. If more presets are to be stored, then the implementation of the method can repeat, commencing at step 505. When, for example, all presets have been stored, the implementation of the method terminates at step 555. Presets, once stored, can be recalled, for example, according to a medical procedure to be performed, by pressing a preset number button on the user interface according to an illustrative embodiment. Returning to Table 1, the percent air setting and the percent water setting set forth therein may be directed to one or more fluid outputs (cf. 380 of FIGS. 5, 5*a* and 7) at pressures ranging from about 5 pounds per square inch (psi) to about 60 psi and at flow rates ranging from about 0.5 liters/minute to about 20 liters/minute. A liquid (e.g., water) may be directed to one or more of the fluid outputs 380 at pressures ranging from about 5 psi to about 60 psi and at flow rates ranging from about 2 milliliters (ml)/minute to about 100 ml/minute. In other embodiments, the air flow rate can go as low as about 0.001 liters/minute, and/or the liquid flow rate can go as low as about 0.001 ml/minute. In certain implementations, a water flow rate through a water line disposed in the electromagnetic energy hand piece may be about 84 ml/minute (e.g., 100%), and an air flow rate through an air line of the electromagnetic energy handpiece 220 (FIG. 4) may be about 13 liters/minute (e.g., 100%). These values may be understood in reference to such flow rates or to other flow rates suggested in the incorporated Waterlase® User Manual or otherwise known to those skilled in the art in the same context.

In accordance with an aspect of the present invention, the storing of one or more combinations of values, in whole or in part, as presets, may enable an end user to switch among the presets, for example, during an operation thereby permitting the end user to quickly and reliably accomplish multiple procedures of a given operation. Efficiency may be increased along with accuracy, such as in the context of relatively complex operations that implement combinations of short-pulse mode procedures and long-pulse mode procedures.

Figure 9:
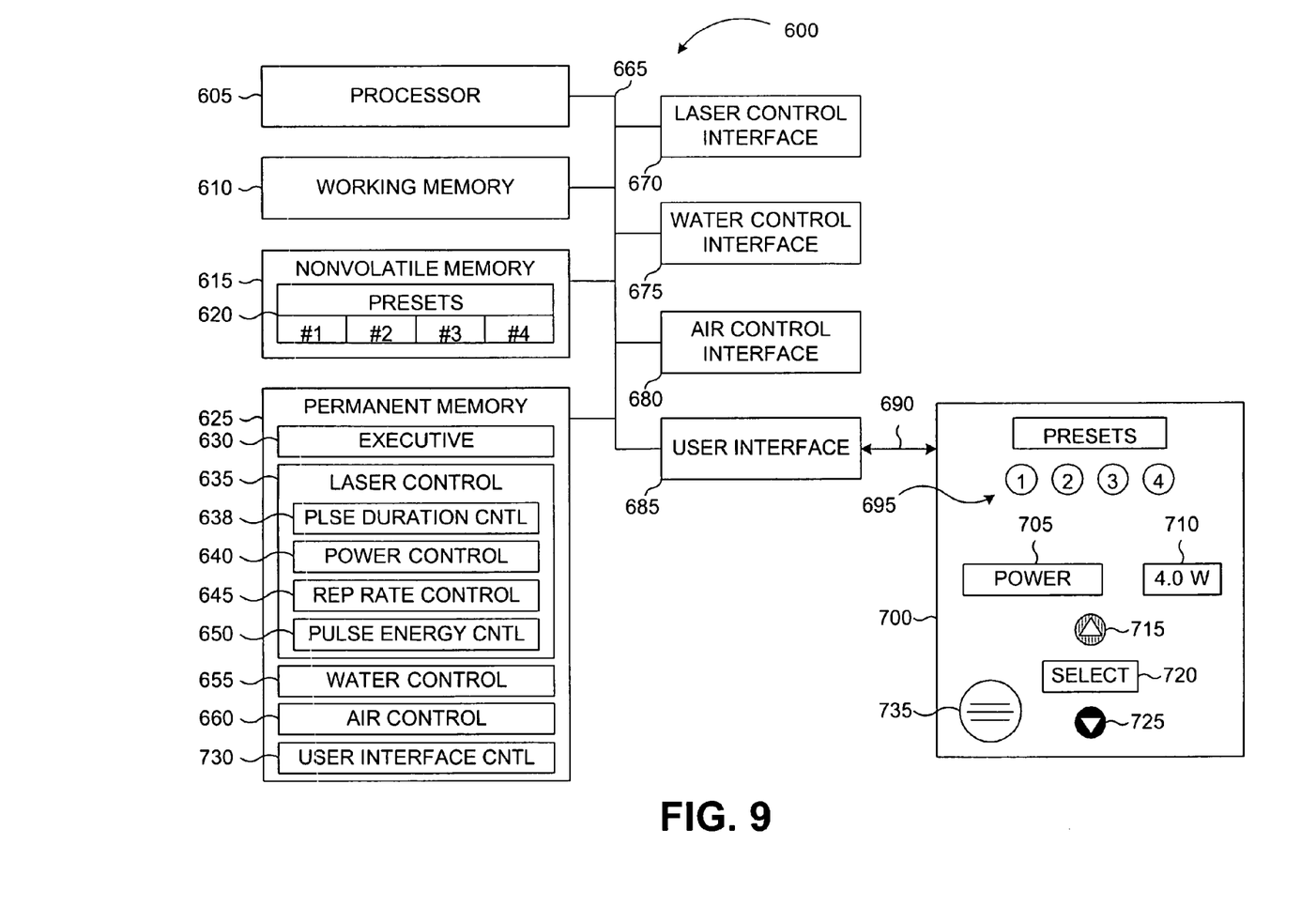
FIG. 9 is a block diagram of an embodiment of a medical electromagnetic energy controller capable of modifying and saving presets according to the present invention.

FIG. 9 is a block diagram of an exemplary embodiment of a medical electromagnetic energy (e.g., laser) controller 600 capable of modifying and saving presets according to an aspect of the present invention. The illustrated embodiment, which may be disposed, for example, in an electromagnetic energy base unit 230 (FIG. 4), comprises a processor 605 (e.g., a microprocessor), working memory 610, nonvolatile memory 615, permanent memory 625, and a user interface 685. The embodiment further comprises an electromagnetic energy (e.g., laser) control interface 670, a water control interface 675, and an air control interface 680. The aforementioned elements of the embodiment are interconnected by a system bus 665 that facilitates communication among the elements. The illustrated embodiment further comprises a user input panel 700. In some embodiments, the processor 605, the working memory 610 (e.g., random access memory (RAM)), the nonvolatile memory 615, the permanent memory 625, and other system elements, such as a clock (not shown), may be implemented on a single microcontroller chip as an application-specific integrated circuit (ASIC). In other embodiments, the electromagnetic energy control interface 670, the water control interface 675, the air control interface 680, and user interface 685 further may be implemented on the same chip. In yet other embodiments, the latter four elements may be implemented on a companion chip to the microcontroller chip. These and other equivalent implementations are contemplated by the present invention.

The nonvolatile memory 615 may be configured to have stored therein presets 620. The illustrated embodiment comprises four presets identified as #1, #2, #3, and #4. Default or pre-programmed values for the presets 620 may be stored in nonvolatile memory 615 at a time of manufacture of the medical electromagnetic energy controller 600. However, because they are stored in nonvolatile memory 615, which can be altered, values of the presets can be changed under end-user control. Once changed, the stored preset values are retained in the nonvolatile memory 615, which is capable of maintaining integrity of stored data even in an absence of electrical power being supplied to the medical electromagnetic energy controller 600, The permanent memory 625, which may be programmed at a time of manufacture of an ASIC, for example, may have instruction sequences stored therein that may, when executed by the processor 605, cause the medical electromagnetic energy controller 600 to perform functions according to the present invention. These instruction sequences in the illustrated embodiment can include an executive instruction sequence 630, an electromagnetic energy (e.g., laser) control instruction sequence 635, a water control instruction sequence 655, an air control instruction sequence 660, and a user interface control instruction sequence 730. The electromagnetic energy control instruction sequence 635 may, comprise, as examples, a power control instruction sequence 640, a pulse duration control instruction sequence 638, a repetition rate control instruction sequence 645, and a pulse energy control instruction sequence 650. The permanent memory 625 in this and other embodiments may have stored therein additional instruction sequences related, for example, to electromagnetic energy handpiece functions tangential to or outside of the immediate scope of the present invention. For example, the permanent memory 625 may contain an instruction sequence that controls electromagnetic energy pulse shape according to an end-user input as well as similar types of instruction sequences related to operation of medical electromagnetic energy (e.g., laser) systems. The executive instruction sequence 630 minimally may cause the processor 605 to schedule and coordinate the aforementioned instruction sequences as well as additional instruction sequences not described herein.

According to an exemplary mode of operation, the embodiment of FIG. 9 receives an input from an end user, i.e., an end-user input, on a user communication line 690. The user communication line 690 may be connected to the user input panel 700, which may have disposed thereon a plurality of preset buttons 695, a SELECT button 720, an increment button 715, a decrement button 725 and a speaker 735. A function display strip 705, such as a liquid crystal display (LCD), may display a function chosen according to the SELECT button 720, and a numerical parameter value may be displayed in a value display strip 710. When an end-user input is received on user communication line 690, the user interface 685 may communicate information between the user input panel 700 and the processor 605. For example, the processor 605 may execute the user interface control instruction sequence 730 that minimally may cause the processor 605 to update a display, such as a message presented in the function display strip 705 and/or a value presented in the value display strip 710, according to the end-user input. In particular, the user interface control instruction sequence 730 further may cause the processor 605 to interact with the user interface 685, for example, to modify and store preset values 620 according to inputs provided by the end user. The user interface control instruction sequence 730 further may cause the processor 605 to activate the speaker 735.

Referring again to FIG. 8, and with continued reference to FIG. 9, an end user may, for example, modify and store a set of preset values. The end user may select a present number at step 505 and may press one of the plurality of preset buttons 695 on the user input panel 700. The user interface 685 may receive an input according to the selected preset number on user communication line 690. The user interface 685 further may communicate with the processor 605 according to the end-user input. The processor 605 may execute the user interface control instruction sequence 730 that minimally may cause the processor 605 to update content of the function display strip 705 and the value display strip 710 according to information received from the user interface 685. Similar interactions between the processor 605 and the user input panel 700 may occur according to the user interface control instruction sequence 730 as will be understood by those skilled in the art. Subsequent to selecting a preset number at step 505, the end user may press the SELECT button 720 on the user input panel 700 until, for example, a POWER indication is observed in the function display strip 705 according to step 510 of FIG. 8. The end user then may enter a power setting by, for example, observing a numerical value corresponding to a currently-active power setting in the value display strip 710 and pressing the increment button 715 to thereby increase the power setting. The end user also may decrease the power setting by pressing the decrement button 725. In either case, the end user may continue to press the increment button 715 and/or the decrement button 725 until a desired value for power is displayed in the value display strip 710. The end user may again press the SELECT button 720 to change the content of the function display strip 705 to, for example, PUL DUR (indication, for example, of an electromagnetic energy pulse duration) according to step 513 of FIG. 8. Again, the user interface instruction sequence 730 may cause the processor 605 to present in the value display strip 710 a value currently stored for electromagnetic energy pulse duration according to the selected preset. The end user then may adjust the value displayed in the display strip 710 by pressing the increment and decrement buttons 715 and 725 in a manner similar to that already described.

The end user may continue to initiate updating of parameter values for selected preset numbers according to, for example, steps 515, 520, 525, and 530 of FIG. 8. The user interface control instruction sequence 730 may cause the processor 605 to store updated parameter values in, for example, working memory 610. When the end user completes updating desired parameter values, the end user may press and hold the selected one of the preset buttons 695. The user interface control instruction sequence 730 may cause the processor 605 to execute a timing instruction sequence (not shown), thereby waiting for about 2 to 3 seconds after which time interval the user instruction control instruction sequence 730 may cause the processor to move the updated parameter values to nonvolatile memory 615 and to update content of the selected one of the stored presets 620. The user interface control instruction sequence 730 then may cause the processor 605 to transmit an audible signal (e.g., a beep) to the speaker 735.

Several operations are now described that involve combinations of short-pulse procedures and long-pulse mode procedures. In many cases, for a given operation, values for some or all parameters (e.g. power, pulse repetition rate, etc.) may be different for short-pulse mode procedure as compared to values for long-pulse mode procedures. Although the operations outlined below are described in a context of a cutter, such as a Waterlase® device, operating in distinct short-pulse (cf. FIG. 3(b)) and long-pulse (cf. FIG. 3(a)) modes at different times, it should be understood that modified, but not necessarily interchangeable, implementations can include long pulses interspersed in short-pulse mode pulse sequences and/or can include short pulses interspersed in long-pulse mode pulse sequences. For example, one or more of the below long-pulse mode procedures of a given operation may, as an alternative to a long-pulse mode pulse sequence of only long pulses, implement a long-pulse mode pulse sequence comprising a plurality of alternating long and short pulses (cf. FIG. 3(c)). In the examples that follow, operations that may be implemented using a cutter, such as a Waterlase® device, are elucidated for various operations wherein short-pulse modes may be used for some procedures of a given operation and long-pulse modes may be used for other procedures of the operation. These examples include modification of root canal surfaces, modification of prepared cavity surfaces, modification of root surfaces at or below the gum line (including modifying a prepared cavity surface to enhance bonding and further including desensitizing or otherwise treating an outer root surface), and apicoectomy procedures.

Modification of Root Canal Surfaces

Figure 10:
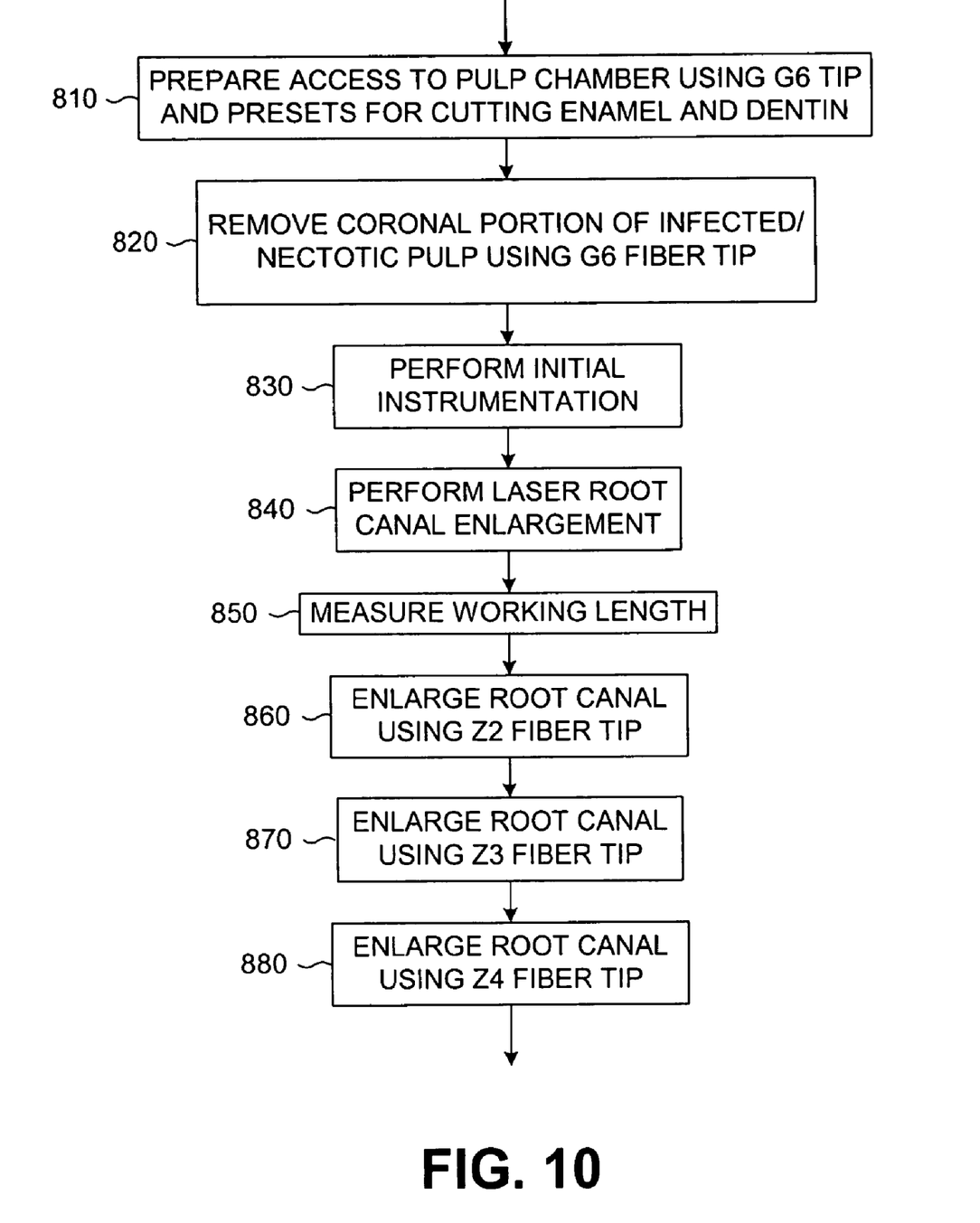
FIG. 10 is a flow diagram outlining a root canal clinical protocol wherein presets may be used in accordance with an exemplary implementation of the present invention.

Appendix C of the incorporated Waterlase® User Manual describes a root canal clinical protocol that is abstracted in FIG. 10. Operating parameters for the procedure as delineated in the incorporated Waterlase® User Manual (e.g., power, pulse repetition rate, energy per pulse, water percentage and/or air percentage, and, as another option, pulse duration) may be entered manually or may be recalled using a preset, such as a preset presented above in Table 1.

In accordance with an aspect of the present invention, a monitor that may form part of the electromagnetic energy base unit 230 (FIG. 4) may instruct use of various output attachments, such as output fiber tips. According to an exemplary implementation, various output attachments are embodied in the form of output fiber tips identified as G6, Z2, Z3, and the like. The monitor may instruct use of the various output attachments at varying times in a given operation or procedure. An embodiment of the present invention may include a visual indication of color codes or topography codes indicative of and corresponding to output tips having a color pattern, various attachments being used at various times, as is more fully described in the above-referenced U.S. Provisional Application No. 60/610,757, filed Sep. 17, 2004, entitled OUTPUT ATTACHMENTS CODED FOR USE WITH ELECTROMAGNETIC-ENERGY PROCEDURAL DEVICE.

In the context of implementing part or all of steps 1-8 of the root canal clinical protocol described in Appendix C of the incorporated Waterlase® User Manual, which steps correspond to steps 810-880 of FIG. 10, a first display on, for example, an electromagnetic energy base unit 230 (FIG. 4) may instruct that the end user prepare access to the pulp chamber at step 810 using a G6 output fiber tip at a setting (manual or preset) of operating parameters appropriate for cutting enamel and dentin. For example, presets #1 and #2 as presented in Table 1 above may be used to prepare access to the pulp chamber. The first display or a subsequent display may instruct that the end user then use the same output fiber tip at step 820 to remove the coronal portion of the infected/necrotic pulp at an appropriate setting of operating parameters. According to one embodiment, the operating parameters may be preset. The same or a subsequent display may instruct that the end user perform initial instrumentation using a Z2 output fiber tip at step 830 using an appropriate setting (manual or preset) of operating parameters. The same or subsequent displays may instruct the end user then to perform, for example, laser root canal enlargement at step 840 using a Z2 output fiber tip. A similar display or displays may instruct the end user to measure working length using a Z2 output fiber tip at step 850 and to enlarge the root canal at step 860 using the Z2 output fiber tip. At step 870 the end user may be instructed by the same or subsequent displays to enlarge the root canal using a Z3 output fiber tip. The same or subsequent displays then may instruct the end user to enlarge the root canal using a Z4 output fiber tip at step 880. All of the preceding displays further may instruct the end user to use appropriate operating parameter settings (e.g., manual or preset values for electromagnetic energy (e.g., laser) power, pulse duration, pulse repetition rate, pulse energy, and settings for water and air).

Steps 810-880 of the root canal clinical protocol described in FIG. 10 may be performed in whole or in part with, for example, a short-pulse mode (wherein the parameters for steps 840-880 may be recalled for the operation using a preset). A before and/or after irrigation step (cf. step 9 in Appendix C of the incorporated Waterlase® User Manual) may include or be preceded by a modification of surfaces (e.g., side-wall surfaces) of the root canal using, for example, the Waterlase® in long-pulse mode to modify (e.g., close) exposed tubule structures or openings. The cutter, which may comprise, for example, a Waterlase® device, may be set (e.g., by the end user activating a preset, or manually) to a power of about 1.5-2 W, a pulse repetition rate of about 30 Hz, an energy per pulse of about 50 mJ, a water setting of about 20%, and an air setting of abut 40%. Surfaces of the root canal may then be modified using a protocol similar to that of steps 840-880. For example, Z2, Z3 and/or Z4 output fiber tips can be successively used for about 5-10 upward strokes each wherein, for example, each upward stroke involves about 5 seconds of lasing and wherein the downward strokes do not entail lasing. In another embodiment, the long-pulse procedure may use only a Z4 output fiber tip, to the exclusion of the Z2 and Z3 output fiber tips.

Modification of Prepared Cavity Surfaces

A cavity is first prepared using, for example, a short-pulse mode (wherein, for example, the parameters, which may be any of those known to those skilled in the art or suggested in the incorporated Waterlase® User Manual, may be recalled for the procedure using a preset, or manually), in combination with techniques suggested in the incorporated Waterlase® User Manual (c.f. Tables 2-6 and related text of the incorporated Waterlase® User Manual) or otherwise known to those skilled in the art. After preparation of the cavity, but before filling thereof, the prepared cavity surface may be modified to, for example, enhance bonding properties. The cutter (e.g., Waterlase®) may be set (e.g., by the end user activating a preset, or manually), to a power of about 2.5-3 W, a pulse repetition rate of about 30 Hz, an energy per pulse of about 80-100 mJ, a water setting of about 10-15%, and an air setting of abut 25-30%. Surfaces of the prepared cavity may then be modified using a circular motion covering all bonding surfaces for a time of, for example, 5-15 sec.

Modification of Outer Root Surfaces at or Below Gum Line

Outer root surfaces can be modified using a long-pulse mode to perform at least one of (1) modifying a prepared cavity surface to enhance bonding and (2) desensitizing or otherwise treating the outer root surface. Either of these operations can be implemented by setting (e.g., via the end user activating a preset, or manually) the cutter (e.g., Waterlase®) to, for example, a power of about 3 W, a pulse repetition rate of about 30-40 Hz, an energy per pulse of about 80-100 mJ, a water setting of about 15-20%, and an air setting of about 40%.

1. Modifying a Prepared Cavity Surface to Enhance Bonding

For operations on outer root surfaces involving modifying a prepared cavity surface to enhance bonding, if a caries is present, for example, on or just below the gum line on the outer root surface, the cutter (e.g., Waterlase®) may be implemented to remove the carious tissue in a short-pulse mode. Short-pulse mode parameters generally known to those skilled in the art or suggested by the incorporated Waterlase® User Manual may be used. According to an exemplary embodiment, the parameters are recalled for the procedure (via a preset, or manually) using techniques suggested in, for example, Tables 2-6 and related text of the incorporated Waterlase® User Manual. After preparation of the cavity on the outer root surface, but before filling thereof, the prepared cavity surface may be modified to, for example, enhance bonding properties. The cutter (e.g., Waterlase®) may be set (e.g., by the end user activating a preset, or manually), to a long-pulse mode and to the settings disclosed in the preceding section entitled Modification of Prepared Cavity Surfaces, and surfaces of the prepared cavity may then be modified using a circular motion covering pertinent bonding surfaces for an exemplary time of 5-15 seconds. In modified embodiments, the short-mode and long-mode pulse procedures may be swapped in time or combined.

2. Desensitizing or Otherwise Treating the Outer Root Surface

For desensitizing or otherwise treating the outer root surface, to the extent exposed, the output fiber tip can be positioned and activated about 2-5 millimeters (mm) from the surface (depending on sensitivity). Lasing can be applied using a circular motion, making sure the patient does not feel pain. In a particular example, lasing may be initiated with the output fiber tip about 5 mm from the surface and, while lasing with a circular motion, the output fiber tip may be brought closer and closer to a distance of about 2-3 mm from the surface while making sure the patient does not feel pain. An s75 output fiber tip, manufactured by BioLase Technology, Inc., of San Clemente, Calif., may be used, and the lasing application time to treat the exposed root surface may be about 30-60 seconds.

To the extent an outer root surface to be treated is not exposed, obstructing gum tissue may be removed in a long-pulse mode by setting (e.g., via the end user activating a preset, or manually) the cutter (e.g., Waterlase®) to, for example, a power of about 1-2 W, a pulse repetition rate of about 40-50 Hz, an energy per pulse of about 20-40 mJ, a water setting of about 0%, and an air setting of about 10-20%. In another embodiment, the cutter may be implemented in a short-pulse mode (wherein, as with the long-pulse mode implementation, parameters known or apparent to those skilled in the art, in view of this disclosure or suggested by the incorporated Waterlase® User Manual, (cf. Tables 2-6 and related text), may be recalled for the procedure via a preset, or manually) using techniques known to those skilled in the art in view of this disclosure or suggested by the incorporated Waterlase® User Manual (c.f., Tables 2-6 and related text). In modified implementations, in the context of the present procedure, either of the two modes can be combined in any sequence or proportion to include, for example, long-pulse mode cutting followed by short-pulse mode cutting, visa versa, and/or treatments using long pulses interspersed in short-pulse mode pulse sequences and/or short pulses interspersed in long-pulse mode pulse sequences.

Apicoectomy Procedures

During cutting of gingival tissue in an apicoectomy procedure as described in Appendix C of the incorporated Waterlase® User Manual, bleeding of the gingival tissue may be attenuated or treated by switching to a long-pulse mode (e.g., via the end user activating a preset, or manually), which, for example, may configure the cutter to a power of about 1-2 W, a pulse repetition rate of about 40-50 Hz, an energy per pulse of about 20-40 mJ, a water setting of about 0%, and an air setting of about 10-20% and/or to combinations of values as disclosed in Table 4 of the incorporated Waterlase® User Manual. Short-pulse mode procedures as set forth in a section of Appendix C discussing apicoectomy procedures may be enabled using presets. With reference to the apicoectomy procedure set forth in Appendix C of the incorporated Waterlase® User Manual, as modified by the disclosure herein, other implementations may comprise either of the two (i.e., long and short pulse) soft-tissue cutting modes being used or combined in any sequence or proportion to include, for example, short-pulse mode cutting followed by long-pulse mode cutting, visa versa, and/or treatments using long pulses interspersed in short-pulse mode pulse sequences and/or short pulses interspersed in long-pulse mode pulse sequences. This disclosure can be extended to other soft tissue procedures, such as frenectomies. As an example of an apicoectomy procedure, a first preset can be activated by the end user to facilitate short-pulse mode incising/cutting, followed by the end user activating a second preset to facilitate a long-pulse mode treatment which may induce, for example, reduced-bleeding cutting or coagulation (via lasing the tissue for about 5-10 seconds), whereby the operation may continue with additional switches to or between one or more of the two (i.e. long-pulse and short-pulse) cutting modes.

Corresponding or related structure and methods described in the following patents assigned to BioLase Technology, Inc., are incorporated herein by reference in their entireties, wherein such incorporation includes corresponding or related structure (and modifications thereof) in the following patents which may be (i) operable with, (ii) modified by one skilled in the art to be operable with, and/or (iii) implemented/used with or in combination with any part(s) of, the present invention according to this disclosure, that/those of the patents, and the knowledge and judgment of one skilled in the art: U.S. Pat. Nos. 5,741,247; 5,785,521; 5,968,037; 6,086,367; 6,231,567; 6,254,597; 6,288,499; 6,350,123; 6,389,193; 6,544,256; 6,561,803; 6,567,582; 6,610,053; 6,616,447; 6,616,451; 6,669,685; 6,744,790 and 6,821,272. For example, output optical energy distributions from the flashlamp 150 of the illustrated embodiment of the present invention may be useful for optimizing or maximizing a cutting effect of an electromagnetic energy source, such as a laser that is driven by the flashlamp 150. The electromagnetic energy output can be directed, for example, into fluid (e.g., an atomized distribution of fluid particles) above a target surface. An apparatus for directing electromagnetic energy into an atomized distribution of fluid particles above a target surface is disclosed in the above-referenced U.S. Pat. No. 5,574,247. The long and/or short pulses can impart large amounts of energy into the fluid (e.g., atomized fluid particles) which preferably comprises water, to thereby expand the fluid (e.g., fluid particles) and apply disruptive (e.g., mechanical) cutting forces to the target surface.

In view of the foregoing, it will be understood by those skilled in the art that the methods of the present invention can facilitate operation of electromagnetic energy devices, and in particular examples medical laser devices exhibiting a capability of producing laser pulses having a plurality of pulse durations. The above-described embodiments have been provided by way of example, and the present invention is not limited to these examples. Multiple variations and modification to the disclosed embodiments will occur, to the extent not mutually exclusive, to those skilled in the art upon consideration of the foregoing description.

For example, a pumping circuit comprising a plurality (e.g., more than two) of high voltage outputs and corresponding pulse-forming networks (e.g., for generating three or more outputs of varying pulse width) is contemplated by the present invention. The present invention may be used with or constructed to implement different electromagnetic energy pulse durations and varying amounts of fluid (e.g., water streams, sprays or mists) in the context of, for example, Erbium-types of lasers, for facilitating, for example, multiple treatment or cutting effects such as hemostatic-type and bleeding-type tissue cutting effects. For example, a wavelength of about 3 μm and pulse durations of 50 μs and 1000 μs may be implemented to provide first and second cutting effects as desired.

The present invention may also be used or constructed with capacitor-charging power supplies in the generation of pulses having variable duration, keeping in mind that such modifications may in some instances present issues such as limited pulse repetition rates, relatively expensive driving circuitry, somewhat rectangular rather than bell-shaped current pulse shapes, and relatively numerous, voluminous and/or heavy capacitors.

While the invention has been described in the context of first and second pulse-forming networks, it is to be understood that greater numbers of pulse-forming networks, each similar to the first and second pulse-forming networks but being constructed for generating pulses of different lengths, are also contemplated. Moreover, while the invention has been described in the context of using a single power supply to generate two pulse outputs for an electromagnetic energy output device, implementations of the present invention using three or more pulse-forming networks may comprise a single power supply or may comprise a number of power supplies that is less than the number of pulse-forming networks.

Additionally, other combinations, omissions, substitutions and modifications will be apparent to the skilled artisan in view of the disclosure herein. Accordingly, the present invention is not intended to be limited by the disclosed embodiments, but is to be defined by reference to the appended claims.

What is claimed is:

1. A method of using a power supply to generate dual pulse outputs for an electromagnetic energy output device, the method comprising:
   providing a first high voltage output —of about 1200-1500 volts from the power supply, the first high voltage output being capable of driving a first pulse-forming network that has a capacitor of about 30-70 μF and an inductor of about 30-70 μH and is configured to generate a first pulse output; and
   providing a second high voltage output —of about 200-500 volts from the power supply, the second high voltage output being capable of driving a second pulse-forming network that has a capacitor of about 300-600 μF and an inductor of about 800-1200 μH and is configured to generate a second pulse output.

2. The method as set forth in claim 1, further comprising providing a pumping source capable of being pumped by at least one of an output from the first pulse-forming network and an output from the second pulse-forming network, wherein the providing of a second high voltage output comprises providing a second high voltage output configured to generate a second pulse output differing from the first pulse output in one or more of duration and power.

3. The method as set forth in claim 2, further comprising:
   generating a pulse having a first duration by pumping the pumping source with the first pulse output; and
   generating a pulse having a second duration by pumping the pumping source with the second pulse output.

4. The method as set forth in claim 3, further comprising generating a plurality of pulses by repetitively pumping the pumping source with the first pulse output.

5. The method as set forth in claim 3, further comprising generating a plurality of pulses by repetitively pumping the laser-pumping source with the second pulse output.

6. The method as set forth in claim 3, further comprising generating a plurality of pulses, each pulse having one of a first duration generated by pumping the laser-pumping source with the first pulse output and a second duration generated by pumping the laser-pumping source with the second pulse output.

7. The method as set forth in claim 6, further comprising:
   receiving a control input from an end user; and
   controlling the generating of pulses according to the control input.

8. The method as set forth in claim 3, wherein:
   the generating of a pulse having a first duration comprises generating a pulse having a duration of about 50 microseconds; and
   the generating of a pulse having a second duration comprises generating a pulse having duration of about 1000 microseconds.

9. The method as set forth in claim 1, wherein:
   the providing of a first high voltage output comprises providing a voltage of about 1500 volts; and
   the providing of a second high voltage output comprises providing a voltage of about 500 volts.

10. The method as set forth in claim 1, wherein the method comprises cutting tissue.

11. The method as set forth in claim 1, wherein the electromagnetic energy output device is a laser that is pumped by the power supply.

12. A method of using a power supply to generate dual pulse outputs for an electromagnetic energy output device, the method comprising:
   Providing a plurality of high voltage outputs from the power supply including at least a first voltage of about 200-500 volts and a second voltage of about 1200-1500 volts; and
   Providing a plurality of pulse-forming networks having capacitors of about 30-70 μF and 300-600 μF and inductors of about 30-70 μH and 800-1200 μH, wherein the plurality of high voltage outputs drives the plurality of pulse-forming networks with signals differing in one or more of duration and power.

13. The method of claim 10, wherein the providing of a plurality of high voltage outputs is performed by providing only two high voltage outputs.

14. The method of claim 10, wherein the providing of a plurality of pulse-forming networks is performed by providing only two pulse-forming networks.

15. The method as set forth in claim 10, further comprising providing a laser-pumping source capable of being pumped by the plurality of pulse-forming networks.

16. The method as set forth in claim 12, wherein the method comprises cutting tissue.

17. The method as set forth in claim 12, wherein the electromagnetic energy output device is a laser that is pumped by the power supply.

18. An apparatus, comprising:
a device having a single power supply capable of supplying a first high potential output at a first potential level and a second high potential output at a second potential level, the first potential level being higher than the second potential level;
a pumping source;
a first pulse-forming network having a capacitor of about 30-70 μF and an inductor of about 30-70 μH and being capable of receiving the first high potential output, the first pulse-forming network further being capable of driving the pumping source with a first signal; and
a second pulse-forming network having a capacitor of about 300-600 μF and an inductor of about 800-1200 μH and being capable of receiving the second high potential output, the second pulse-forming network further being capable of driving the pumping source with a signal differing from the first signal in one or more of duration and power.

19. The apparatus as set forth in claim 18, wherein the device is a laser device and the pumping source is a laser-pumping source.

20. The apparatus as set forth in claim 19, wherein the device is constructed to facilitate cutting of tissue.

* * * * *